United States Patent
Heffelfinger et al.

(10) Patent No.: US 6,750,457 B2
(45) Date of Patent: Jun. 15, 2004

(54) SYSTEM FOR HIGH THROUGHPUT ANALYSIS

(75) Inventors: David M. Heffelfinger, Oakland, CA (US); Aram P. Schiffman, San Ramon, CA (US); Bala S. Manian, Los Altos Hills, CA (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 401 days.

(21) Appl. No.: 09/942,472

(22) Filed: Aug. 29, 2001

(65) Prior Publication Data

US 2003/0044967 A1 Mar. 6, 2003

(51) Int. Cl.⁷ .............................................. G01N 21/00
(52) U.S. Cl. .................... 250/458.1; 250/461.1
(58) Field of Search ................... 250/458.1, 459.1, 250/461.1, 461.2

(56) References Cited

U.S. PATENT DOCUMENTS

| | | | |
|---|---|---|---|
| 4,979,824 A | 12/1990 | Mathies et al. | 356/318 |
| 5,072,382 A | 12/1991 | Kamentsky | 364/413.08 |
| 5,091,652 A | 2/1992 | Mathies et al. | 250/458.1 |
| 5,274,240 A | 12/1993 | Mathies et al. | 250/458.1 |
| 5,547,849 A | 8/1996 | Baer et al. | 435/7.24 |
| 5,556,764 A | 9/1996 | Sizto et al. | 435/7.24 |
| 5,591,981 A | 1/1997 | Heffelfinger et al. | 250/458.1 |
| 5,784,152 A | 7/1998 | Heffelfinger et al. | 356/73 |
| 5,962,238 A | 10/1999 | Sizto et al. | 435/7.24 |
| 6,043,506 A | 3/2000 | Heffelfinger et al. | 250/584 |
| 6,633,375 B1 * | 10/2003 | Veith et al. | 356/237.4 |

* cited by examiner

*Primary Examiner*—Constantine Hannaher
*Assistant Examiner*—Timothy Moran
(74) *Attorney, Agent, or Firm*—Thomas Schneck; David M. Schneck

(57) ABSTRACT

An apparatus and method in which illumination light and collected emitted light share a pathway and subsequently are physically separated. The optical configuration is designed such that at the point of separation, the illumination light is at has a smaller cross sectional area than the collected light. Collected light is directed away from the pathway of the illumination light and to detection optics. This configuration is adaptable to illumination and light collection across a broad wavelength spectrum. This configuration is adaptable to scanning in a limited depth of field to allow high throughput optical analysis of samples.

18 Claims, 6 Drawing Sheets

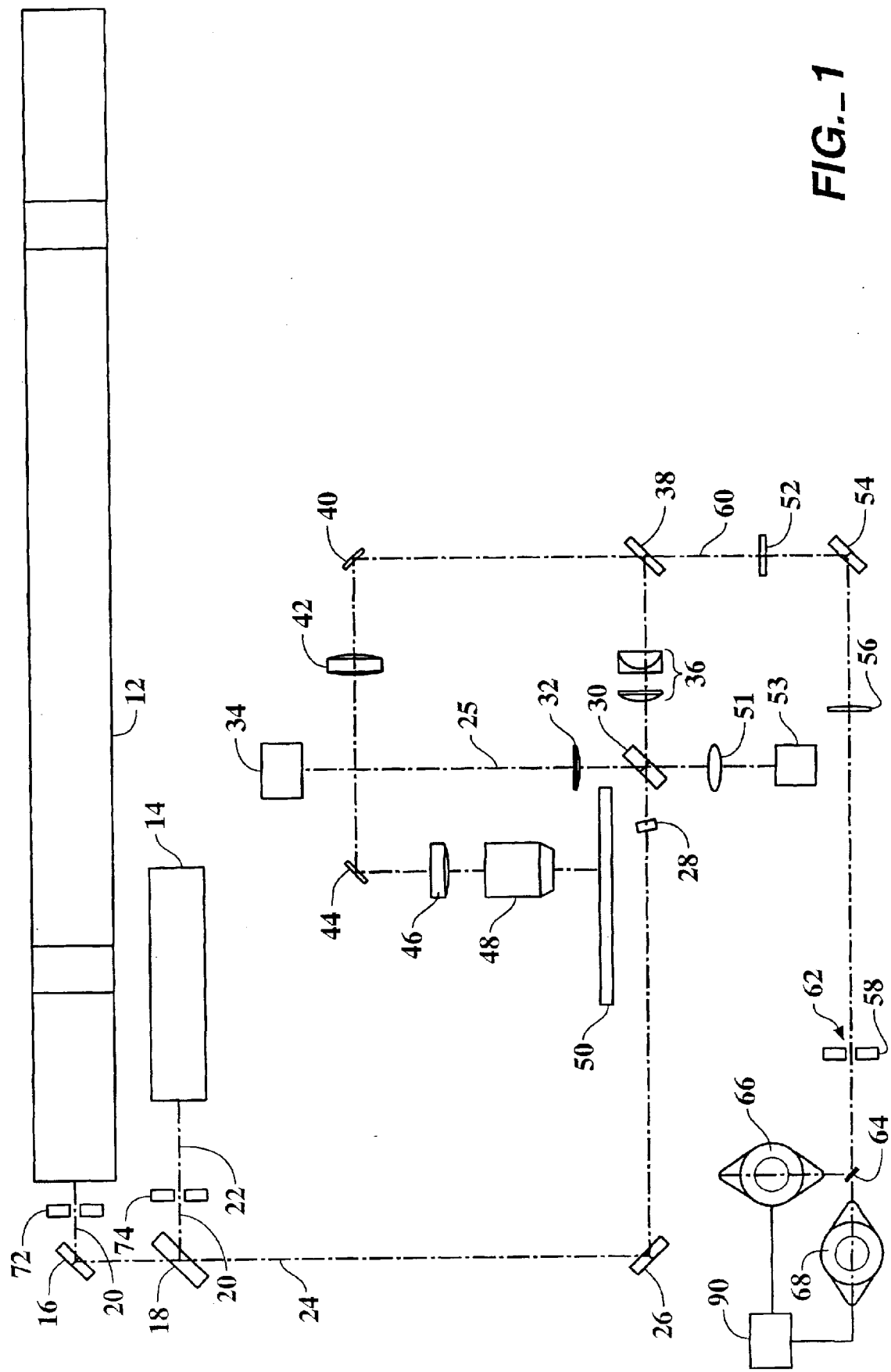
FIG._1

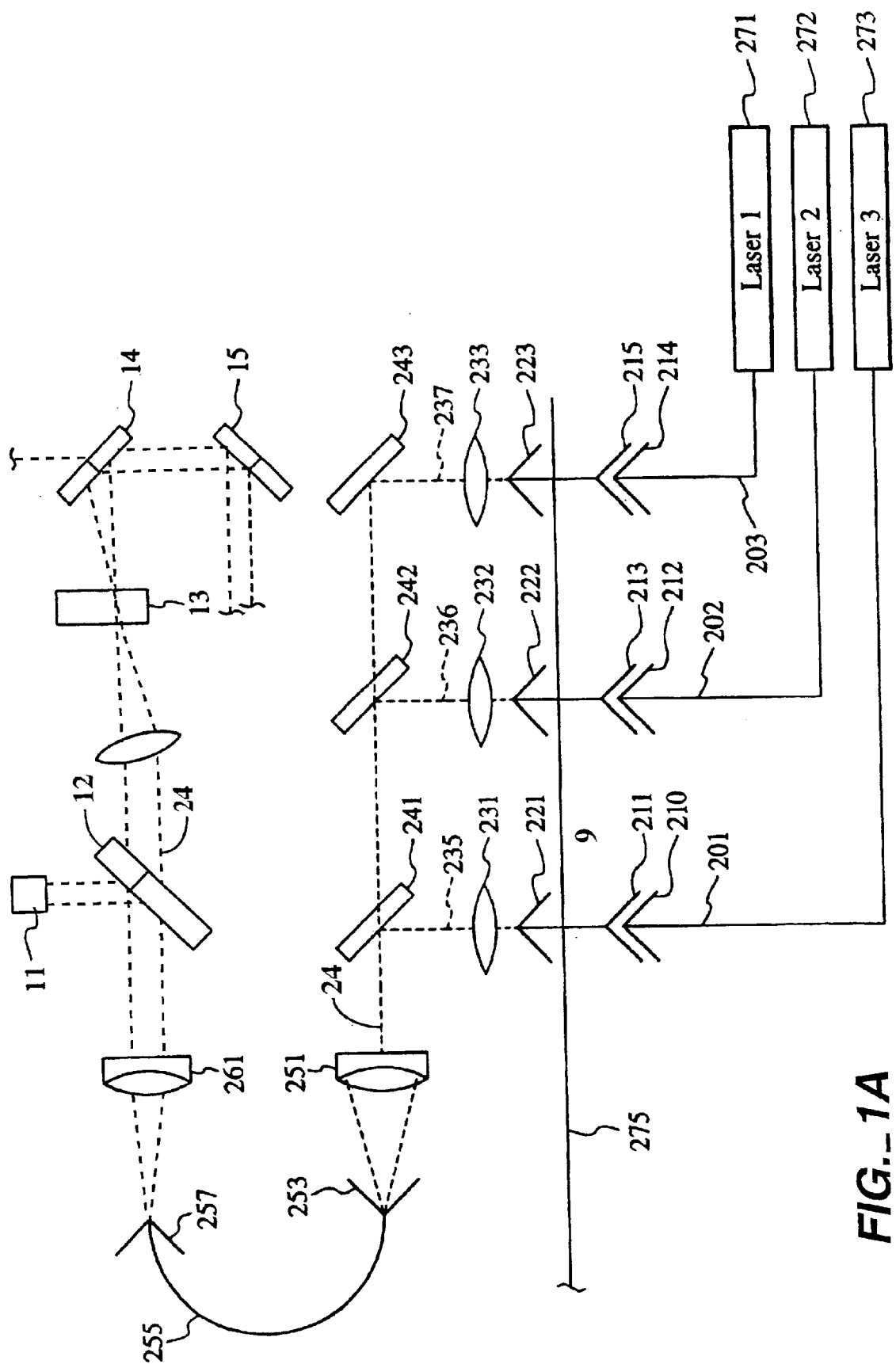
FIG._1A

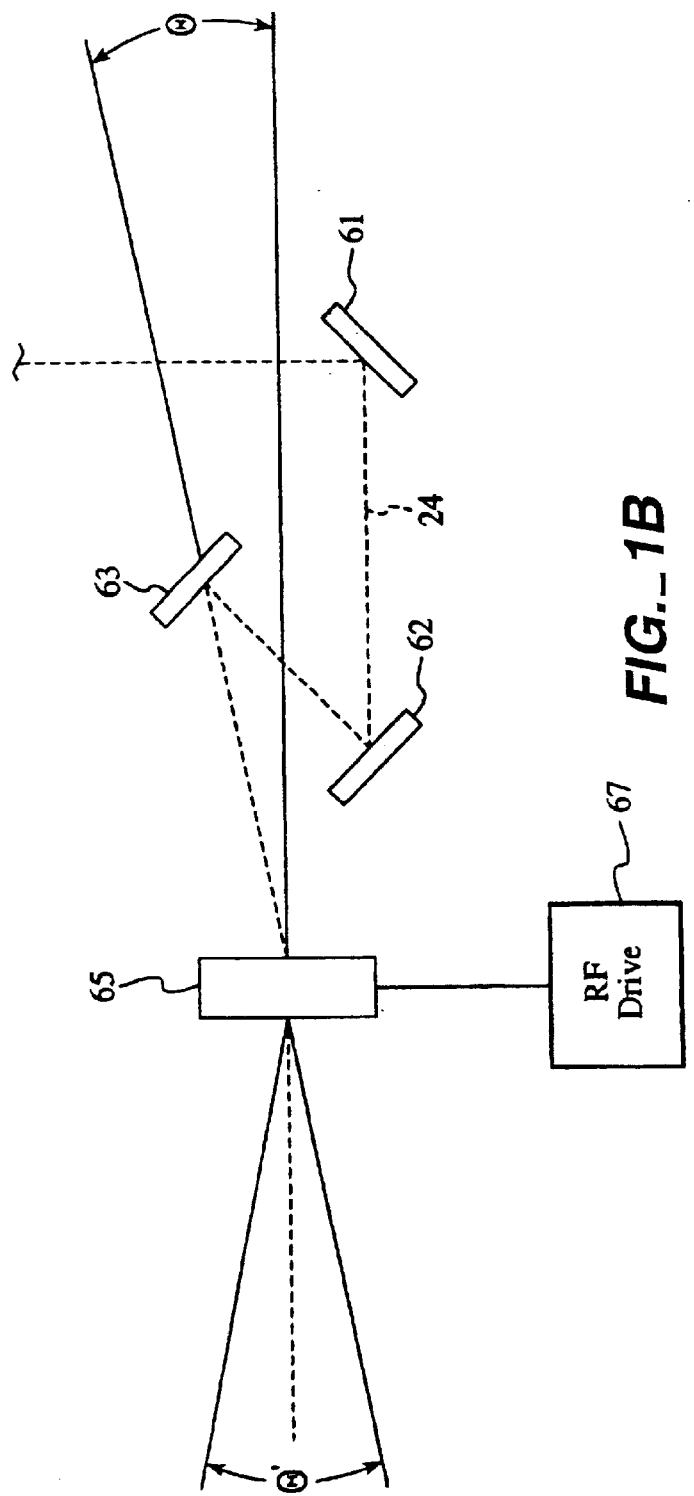
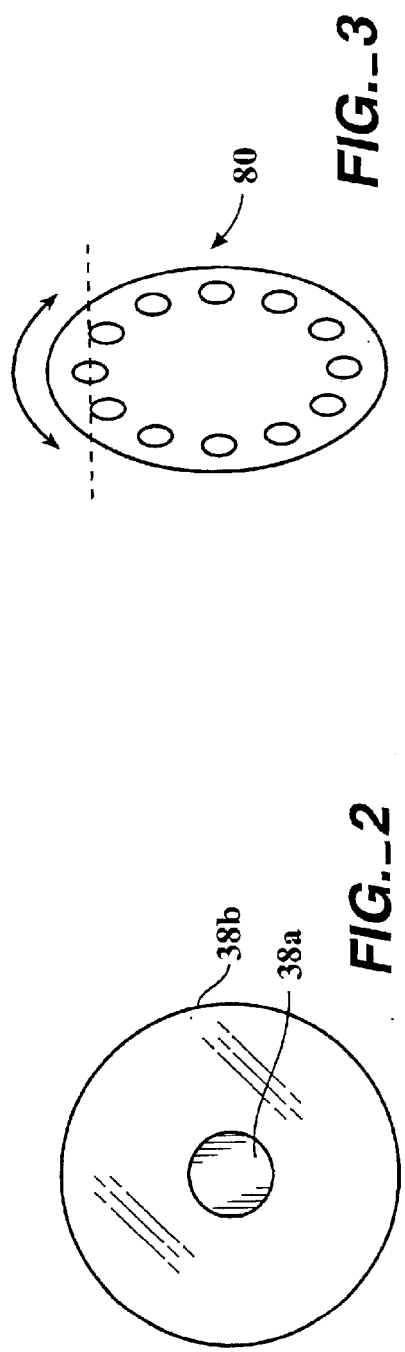
FIG._1B
FIG._2
FIG._3

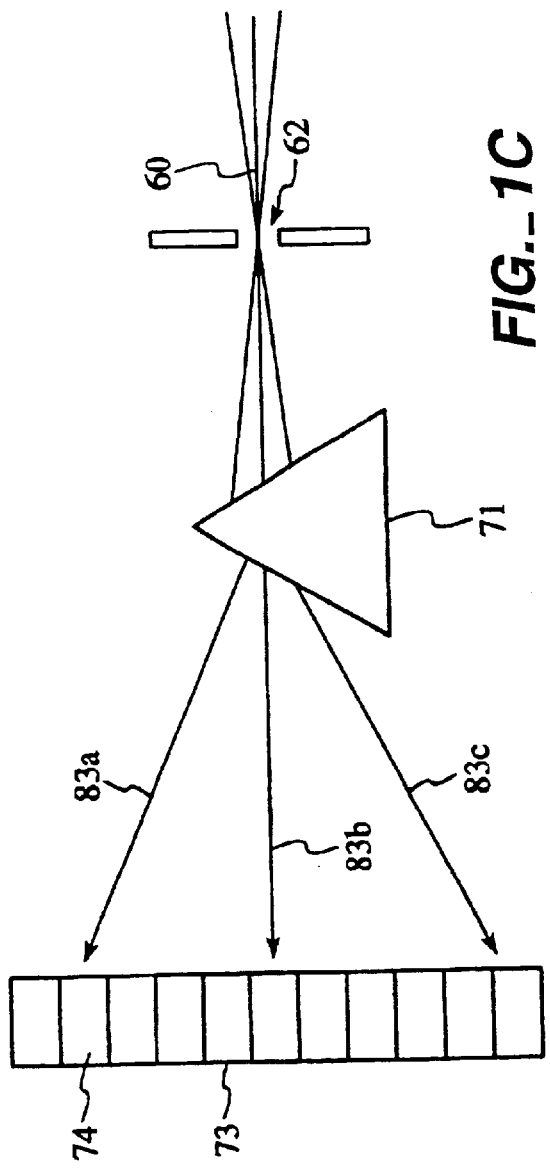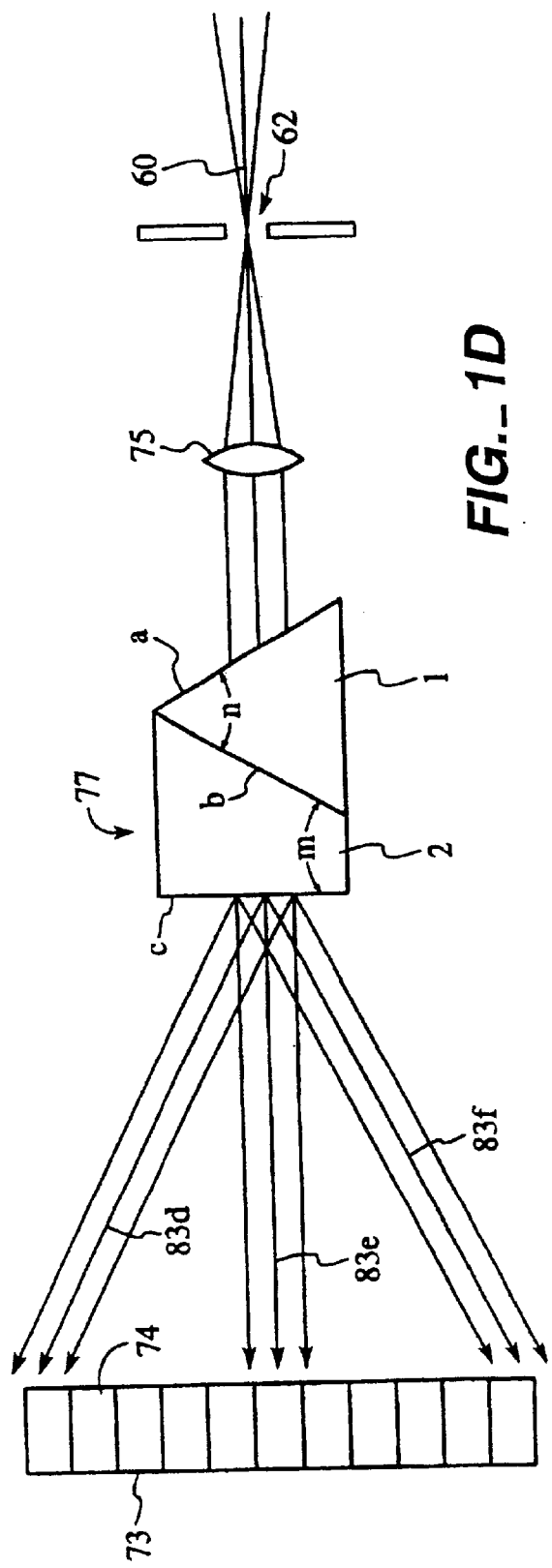

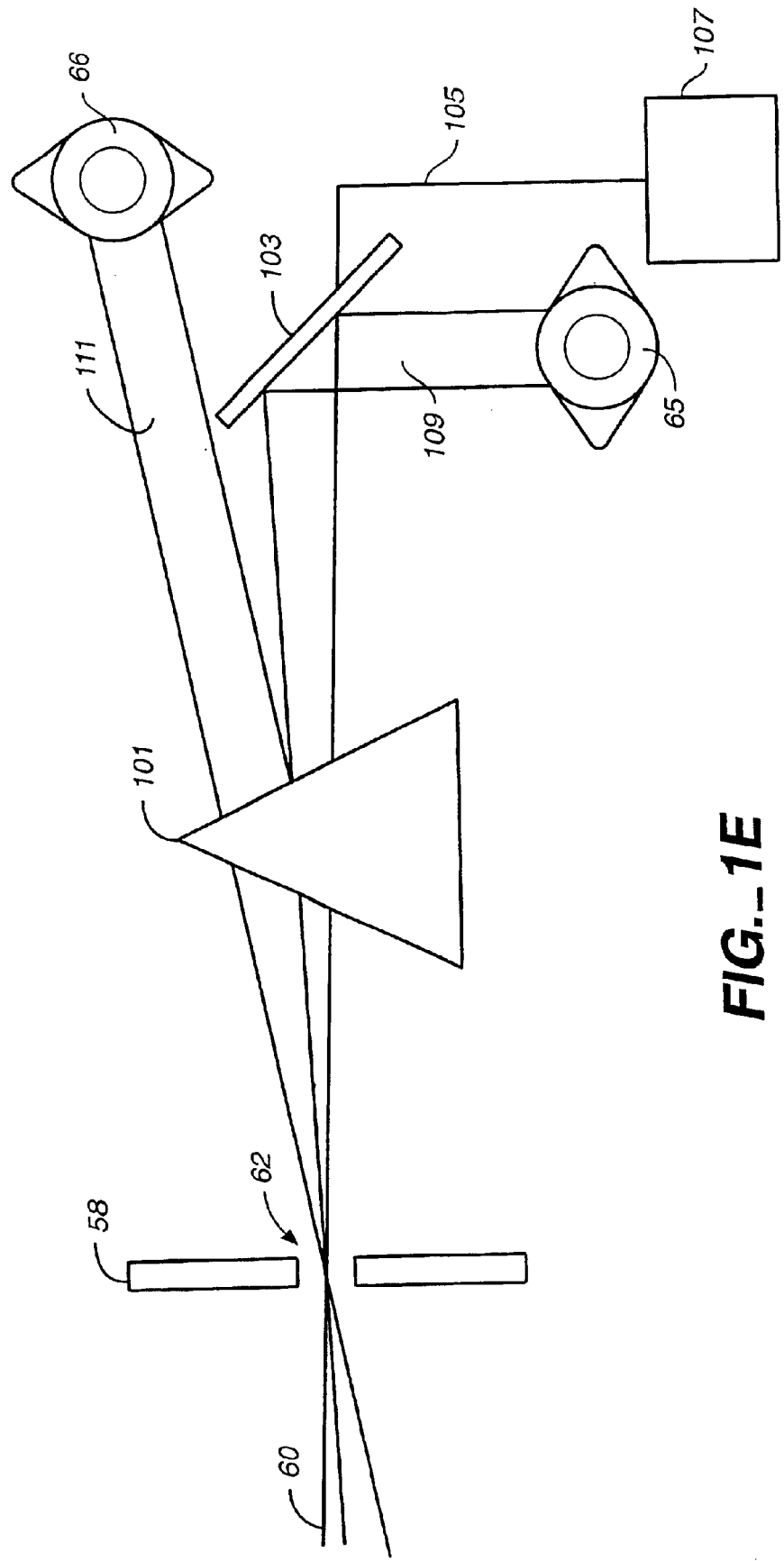
FIG._1E

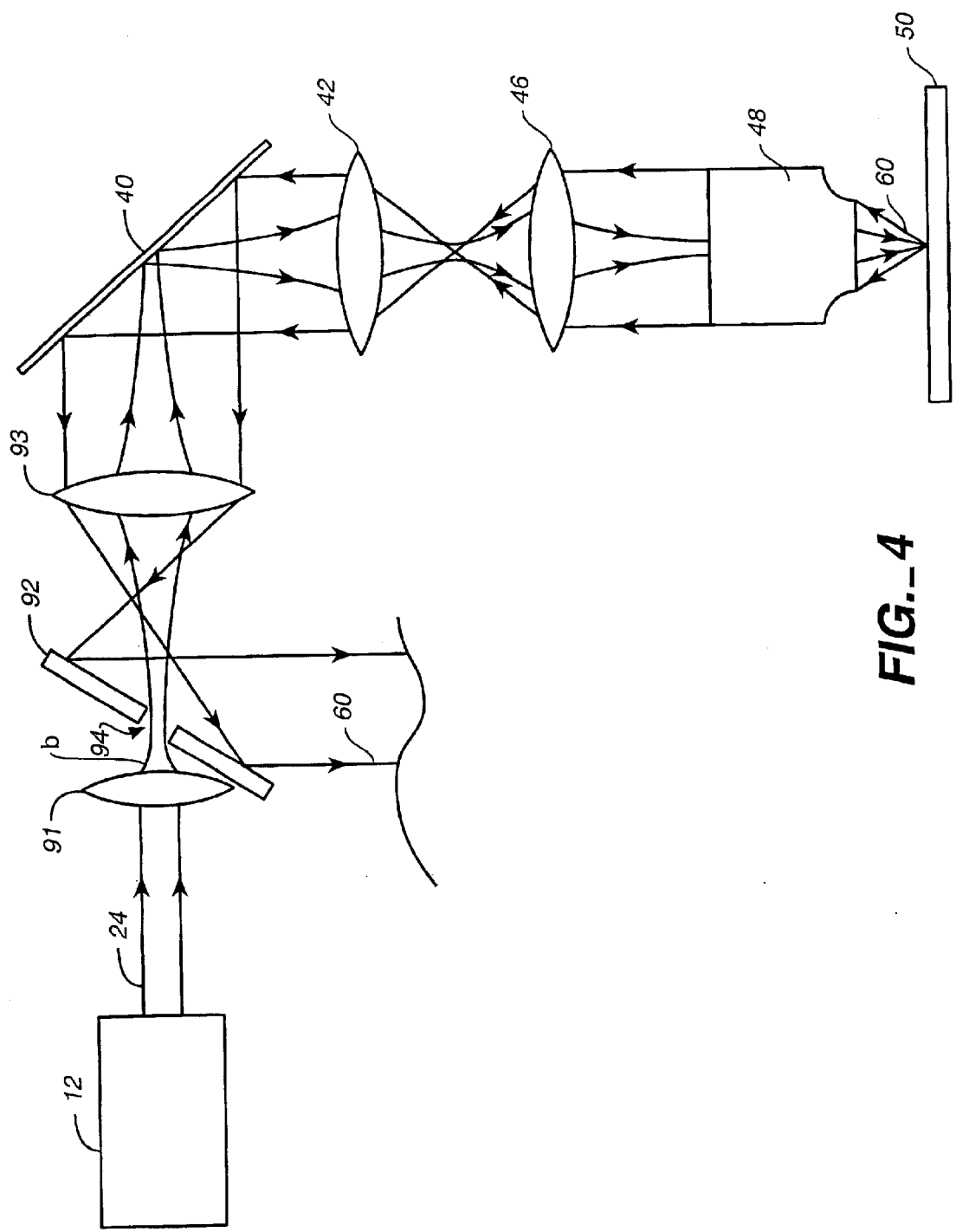
FIG._4

SYSTEM FOR HIGH THROUGHPUT ANALYSIS

CROSS-REFERENCE TO RELATED APPLICATIONS

This is related to application U.S. Ser. No. 09/318,494 which is a continuation-in-part of U.S. Ser. No. 08/698,807 filed Aug. 16, 1996 which is a continuation in part of U.S. Ser. No. 08/018,762 filed on Feb. 17, 1993. The present application is also related to U.S. Pat. No. 5,556,764 invented by Ning L. Sizto and Louis J. Dietz, filed on the same day as U.S. application Ser. No. 08/698,807 and owned by the same Assignee. The related application is incorporated by reference as if fully set forth herein.

TECHNICAL FIELD

This invention relates to optical detection instruments more particularly optical detection systems that may illuminate, collect and detect light of a broad spectral range of wavelengths.

BACKGROUND OF THE INVENTION

In chemical, biochemical and cellular analytical systems, imaging provides a powerful tool. The imaging may use fluorescence, luminescence (e.g. chemiluminescence) or radio labels in a large number of analytical procedures. This imaging allows very sensitive detection. The use of such labels is well characterized, for example as detection agents conjugated to probes or binding agents. Alternatively the label may be directly incorporated into a target of interest. The sensitivity of these labels allows detection of rare events and rapid sample analysis. Optical analysts may be applied to a number of different analytical applications including identification of compounds, assay of array of biomolecules (e.g. biopolymers) or assay of binding events (e.g. competitive binding).

The benefits of imaging technology have led to widespread application of this technology to research needs. One benefit of optical screening has been in increased throughput. The speed and sensitivity of optical scanning is adaptable to automated high throughput assays that are required for screening large numbers of samples against numerous interaction agents.

Developments in the fields of genomics, cytology and chemistry have produced challenges for the evaluation and analysis of large numbers of unique samples, compounds or biological isolates.

For example, in the field of genetics, the human genome project and other genome sequencing efforts have identified tens of thousands of unique oligonucleotide sequences. Screening of gene expression against these known sequences would provide information on gene expression and regulation. This information could be correlated with disease states or applied to evaluate response of cells to therapeutic treatment (e.g. for clinical evaluation of potential pharmaceutical evaluation, monitoring of response to therapy, etc.). Labeled mRNA or cDNA isolated from cells could be used in expression evaluations. Alternatively, genomic fragments may be screened against known sequences to determine homology between the screened DNA and known genes.

Clinical evaluation of DNA expression could require analysis of DNA from hundreds of thousands of individuals. This analysis could involve screening of nucleic acid isolations from hundreds of different cell types against tens of thousands of unique oligonucleotide sequences. The present need for throughput has motivated the development of multiplexed, automated, high throughput analysis of nucleic acid homology.

There is no single, standardized technology for nucleic acid analysis. In part this is a result of the differing throughput needs. The density of analytical arrays or the scale of separation analysis of DNA will depend on the amount of samples that are being analyzed. Gene expression analysis may be performed in wells on a multiwell plate, on a separation gel, on a chip substrate containing an array of reaction spots or using other formats. If a separation gel or chip substrate is used, the separation substrate may either be read directly or transferred to another substrate, (e.g. a transfer [blotting] membrane). Alternatively, an emitted signal from an assay of samples (e.g. chemiluminescent signal, radio signal) may be recorded on a storage device (e.g. a storage phosphor screen), which is subsequently analyzed. The samples of interest may be detected by detecting a signal associated with the sample.

In addition to the label and substrate variability, the sample size may vary. This may range from the relatively large target from a separation gel to a spot on a chip array, which may be orders of magnitude smaller. Presently, most automated analytical systems are limited in types of substrates and target densities that the system is able to analyze. The data from different analytical systems often must be subsequently combined to make a finalized evaluation of a biological sample or compound.

High throughput analysis ability is required to analyze sample nucleic acids using known sequences to study genetic variation, differential expression, etc. High throughput systems have taken advantage of automation to increase sample analytical rate. Optical analytical systems may further increase sample processing throughput by designing systems with multiplex capability. For example, the ability to distinguish multiple dyes at a single dye location allows a number of dyes, each associated with a unique probe or binding agent to be used in a single assay. The combination of markers may be used at a single target loci and distinguished by the analytical system by the unique dye emission wavelength profile. This further increases the information gained from each analytical scan and increases analytical throughput. However, this would only be possible in an analytical system in which the illumination and detection optics were adapted for use with a number of different emission profiles and could operate over a wide spectral range.

In a number of scanning fluorescent analytical instruments, the excitation light and the generated fluorescent emission share a pathway and must be optically separated. Some mechanism is needed to separate an excitation laser beam from a spectrally shifted collinear, counter propagating collected fluorescent light. Typical systems use a dichroic mirror to reflect wavelengths of the laser light and transmit wavelengths of the emission light. One example is seen in Baer et al. (U.S. Pat. No. 5,547,849). A laser produces coherent light that is directed onto a dichroic mirror. The mirror directs light of the wavelengths produced by the laser through an objective lens and onto a sample. The focused beam waist is directed onto a layer to be scanned. The emitted fluorescent light is collected by the objective lens and transmitted as a collimated retrobeam to the dichroic mirror. The mirror is selected to transmit the wavelengths of the collected fluorescent light to detection optics. An alternative system is seen in Kamentsky (U.S. Pat. No. 5,072,382). In this system a laser produces an illumination beam that is directed through a dichroic mirror and onto a focus lens. The focus lens focuses the illumination light onto a sample, exciting fluorescence. The lens collects excited fluorescent light, which is transmitted as a retrobeam to the dichroic mirror. Light of the fluorescent wavelengths is reflected by the mirror onto detection optics.

These arrangements allow the rapid scanning of a sample and detection of emitted light. However, these systems have several significant drawbacks. First, the coatings on dichroic mirrors may be angle sensitive when the coatings must filter or reflect multiple sets of wavelengths. A slight variation in angle can result a significant change in the wavelengths transmitted and reflected by the mirror coating. In such cases, the positioning of the mirror must be precise for proper functioning. Second, the coatings are designed to transmit and reflect specific spectral bands. This severely limits the illumination and emission wavelengths that may be used in the optical scanning system. Changing the excitation laser wavelength or the fluorescent dye (having an alternative emission profile) would require replacement of the dichroic mirror. For any one dichroic mirror, the system is locked into specific wavelength choices. Third, the coatings that are designed to transmit or reflect multiple excitation wavelengths must still be selected for specific wavelength bands. It is common that the excitation wavelength will encroach on an emission profile of a fluorescence dye. Since the dichroic mirror transmits only a selected range of wavelengths, some emission intensity outside of this range is lost. The separation of excitation and emission wavelengths may result in a substantial loss of the collected fluorescence due to the dichroic mirror not transmitting some emission light to the detectors.

Versatility in analyzing various analytical substrates is also important to maximize the utility of optical analytical systems. Presently, a number of different substrates are used to analyze bio-molecular samples. These include gels, microplates, membranes, arrays (disposed on plastic, glass or membranes) storage phosphor screens storing radiant energy images from various samples and other devices. At present, optical analytical systems are generally designed for analysis of a single type of device. The elements of an analytical device, such as the reading stage and the focusing optics are generally selected to be used with a single sample type. In many optical analytical systems fixed illumination optics determine an illumination geometry, limiting the range of targets sizes which may be illuminated by a single system. As applied this has meant that different analytical systems must be used for different analytical targets. An analytical system would have increased utility if the system were adaptable to a range of target sizes and target densities. This would allow a single analytical system to scan a number of different sample types and sample densities.

A number of different optical readers have been developed to provide technology to meet imaging needs. U.S. Pat. No. 6,043,506 describes an optical scanner in which optical fibers are fixed into a scan head for illumination and/or collection of light from a sample. The scan head is moved by a transfer gantry to scan the head in two dimensions over a sample surface. To ensure the scan head is operating within the desired parameters of the system, the scan head is moved to a separate calibration location prior to each scan. Although some control of the resolution of the scanning system is possible (e.g. by limiting the scanning geometry by finer graduated steps of the scan head), the fixed optics of the scan head provides a limit to the resolution of the scan system.

U.S. patents granted to Mathies et al. are also relevant to the field of the present invention. In U.S. Pat. No. 4,979,824, an optical analytical apparatus is described. This apparatus is based on a flow cytometry system and utilizes a spatial filter to define a small probe volume that allows for detection of individual fluorescent particles and molecules. Laser power and exposure time of the sample are selected to enhance signal-to-noise ratio. Real-time detection of photon bursts from fluorescent particles is used to distinguish the number, location or concentration of the particles from background energy.

In U.S. Pat. No. 5,091,652 to Mathies et al., a laser-excited fluorescent scanner is enclosed for scanning separated samples using a confocal microscope. Generally, the sample is separated on a slab gel by electrophoresis. The gel is subsequently optically analyzed. Alternatively, the sample may be analyzed on a membrane, filter paper, petri dish, or glass substrate. The confocal microscope directs an illumination laser beam into the sample with beam oriented so that background scattering is minimized by the polarization characteristics of the scattered light.

U.S. Pat. No. 5,274,240 also granted to Mathies et al. and a continuation-in-part of the above patent, teaches a capillary array scanner. This invention is primarily intended for fluorescence detection from a plurality of in-line capillary tubes containing samples that have been separated by capillary electrophoresis. The fluorescence detection assembly employs a confocal system to detect fluorescence from the interior volumes of each capillary tube.

U.S. Pat. No. 5,784,152 discloses an optical scanner for analyzing multiwell plates, gel plates, or u storage phosphor screens. The sample is illuminated with focused light that is "tuned" by filters to a selected illumination wavelength. The detection is also "tuned" by filters or other optical devices to allow for light detection at a selected wavelength. For both illumination and detection a bandpass filter is used as a primary wavelength selector. As with the prior referenced system, the system resolution is both fixed and fairly limited. The plate or gel is scanned by two-dimensional movement of the stage or illuminating light.

U.S. Pat. No. 5,591,981 discloses a method and apparatus that provides continuous tuning of excitation and/or emission in fluorescent imaging. For both illumination and detection, dispersive elements or filters are used to produce spectral shifts to transmit a selected wavelength range. A non-coherent, broad wavelength lamp is focused to illuminate the sample. The emitted light passes through a filter on a filter wheel and an interferometer. The light emission then passes onto a charge coupled diode detector. The detection system is tuned to different settings to allow individual, one-at-a-time detection of individual dyes.

In these optical systems, fixed sample scanning optics limit the system to relatively narrow ranges of detection resolution.

The scanning mechanism of the optical system impacts the throughput potential of the system. Movement of a scan head requires additional scan time, requires additional calibration and requires additional motor parts that increase system size. Transmission and collection of multiple wavelengths in optical fibers limits resolution. The optical transmission fiber diameter must be sufficient for multimode propagation if multiple wavelengths are transmitted through the fiber. Light may lose coherence when the light is propagated through multiple fibers. If the wavelengths are not aligned into various fibers (due to varying fiber length) the beam may lose Gaussian properties. In some systems, the use of long pass filters in conjunction with each detector limits each detector to detect a single wavelength intensity measurement.

It is an object of the invention to provide a reader for the optical analysis of a number of different substrates, including chip arrays, microplate wells, cells within microplate wells, gels and storage phosphor screens. It is a further object to allow the illumination and detection to be selectable across a number of wavelengths. It is a further object of the invention to be able to detect at a plurality of resolutions, including detection of discrete targets 1–100 um in width. It is a further object to enable detection of a greater number of dyes than detection channels used.

SUMMARY OF THE INVENTION

The objects are achieved with an optical analytical system that scans in a limited depth of field. The system allows illumination and detection at selectable wavelengths while also allowing for selectable resolution of detection. In this system, a selected set of one or more lasers provide excitation illumination. If multiple illumination sources are used, the beams may be optically combined into a single illumination beam or used individually. Separate optics split the illumination beam, diverting part of the beam into a beam detector that monitors beam output and power fluctuation. A selectable laser line filter is used with each laser to filter out wavelengths other than the selected laser wavelength.

The illumination beam may be directed through a zoom contractor/expander optic that shapes the beam spot. This multi-element lens is focused to shape the illumination beam, producing a beam spot of a selectable size at the targeted sample location. The beam spot size is selected to concentrate energy into a limited depth. This would allow optimized scanning of different density arrays. After passing through the beam expander/contractor optic, the beam is directed by a scanning optic that produces a beam scan in a first direction dimension. A galvo mirror, resonant scanner, rotating polygonal mirror, or acousto/optic scanner, or other scanning optic may be used to effect the beam scan. The focused scanned beam is directed onto the sample.

The emitted light is collected and sent to the detection optics. The objective acts as a wide angle light collector that collects light and transmits the light as a retrobeam to the detection optics. The excitation beam and emission light are separated using an optical element having a central optic, that directs the illumination light to the sample, surrounded by an annular optic that directs the collected emission light to the detection optics. This could be effected by a central broadly reflective mirror annularly surrounded by a transmissive material that allows collected emission light to pass to the detection optics. In another embodiment, a central hole in a broadly reflective mirror allows the illumination beam to pass through the illuminate the sample. The collected fluorescent light beam is radially much larger than the illumination beam. The collected retrobeam is reflected by the mirror onto detection optics.

In the present invention the beam focusing optics allow the system to be used to analyze a range of sample densities present on a number of different types of substrates. In one embodiment, the arrays are present on the bottom of multiwell plates. Autofocus mechanisms allow rapid focus onto the bottom of multiwell plates or other analytical substrates. Alternatively, storage phosphor screens may be scanned. The storage phosphor screen records the signal emitted from either a luminescent or radioactive label.

BRIEF DESCRIPTION OF THE DRAWINGS

FIG. 1 is a plan view of an apparatus according to the present invention.

FIG. 1A shows a plan view of a fiber optic link used to provide the excitation beam of FIG. 1.

FIG. 1B shows a plan view of an acousto-optic scan assembly.

FIG. 1C shows a plan view of a dispersive prism used with a segmented detector as the detection means of FIG. 1.

FIG. 1D shows a plan view of a direct vision prism used with a segmented detector as the detection means of FIG. 1.

FIG. 1E illustrates a prism detector with variable wavelength cutoff.

FIG. 2 is a dot mirror used to reflect the illumination beam and transmit the emission light to the detectors.

FIG. 3 is a filter wheel.

FIG. 4 illustrates a beam pass-through mirror used to transmit the illumination beam and reflect the collected emission light onto detectors.

DETAILED DESCRIPTION OF THE INVENTION

With reference to FIG. 1, a first laser 12 emits laser light 20 that is directed by steering mirror 16 through beam combiner (e.g. dichroic mirror) 18. A second laser 14 directs a second laser light 22 to beam combiner 18. Shutters 72, 74 are positioned in front of each laser 12, 14. The shutters are separately controlled such that either shutter may be selectively closed, blocking one laser from transmitting light to beam combiner 18. Beam combiner 18 combines first laser light 20 and second laser light 22 into illumination beam 24.

FIG. 1A provides an alternative for combination of illumination sources. In FIG. 1A, light is provided by lasers 271, 272, 273. Each laser can produce light at a different wavelength. The lasers are arranged such that laser 271 produces light with a relatively long wavelength, laser 272 has an intermediate wavelength and laser 273 has the shortest wavelength. Lasers 271, 272, 273 focus light into optical fibers 203, 202, 201 respectively. Optical fibers 203, 202, 201 each terminate in a respective fiber connector output 214, 212, 210. Each of fiber connector outputs 214, 212, 210 may be removably coupled to fiber connector inputs 215, 213, 211. Optical fibers 219, 218, 217 extend into the optical scanner. It is apparent from this arrangement that any of lasers 271, 272, 273 may be coupled to the optical scanner allowing each laser to be used either alone or in combination. In addition, exchange of lasers is greatly simplified. The fiber connector output can be easily decoupled from the fiber connector input to allow for simplified exchange of lasers.

The preferred wavelengths for use with the optical scanner may be in the 300 nm–1100 nm range. The optical fibers used with each laser may be adapted to have single-mode light propagation with the guided mode selected to correspond to the light wavelength produced by the corresponding laser. The fiber connector input and fiber output connectors are selected to allow removable coupling of optical fibers into the system. A connector that encases the fiber in a ferrule and holds optical fibers in face-to-face abutment with a threaded fiber locking mechanism is one possible connector. A high-precision ceramic ferrule connector with antirotation key may alternatively be used as the connector. This type of connector minimizes insertion losses when coupling single mode fibers.

Fiber connector outputs 223, 222, 221 extend the optical fiber through the system casing 275 and project the light from their respective fibers onto respective collimating lenses 233, 232, 231 which collimate the output light into collimated beams 237, 236, 235 respectively. Beam 237 is directed by steering mirror 243 to dichroic mirror 242. Dichroic mirror 242 is selected to allow the relatively longer wavelength light produced by laser 271 to be transmitted. While collimated beam 237 passes through dichroic mirror 242, collimated beam 236 generated by laser 272 is of a shorter wavelength that is reflected by dichroic mirror 242. In this way, collimated beams 237 and 236 may be combined. In a similar manner, dichroic mirror 241 transmits longer wavelength light of collimated beams 236, 237 but reflects shorter wavelength light of collimated beam 235 thereby combining collimated beams 235, 236, 237 through use of a multi-mirror dichroic stack. The illustrated embodiment is one method to combine beams. Other technology for beam combination is known in the art.

The collimated beams 235, 236, 237 are combined to form excitation beam 24. Excitation beam 24 impinges upon achromatic coupling lens 251 which focuses the beam into fiber connector input 253 on one end of optical fiber 255. Excitation beam 24 is transmitted through optical fiber 255 to fiber connector output 257 that projects the light from optical fiber 255 onto collimating lens 261. Optical fiber 255 is selected to have a fiber core sufficiently large or length sufficiently short to support the wavelengths of excitation beam 24 in guided mode. This light will generally have a wavelength between 300–1000 nm. A small core, single, or multimode optical fiber could accommodate this wavelength range.

Excitation beam 24 is collimated by collimating lens 261 and directed through glass plate 12 which optically communicates with power monitor 11. After passing through glass plate 12, excitation beam 24 then passes through laser line filter 13 and through spectral dispersion means 14 which acts as a mirror for the excitation beam wavelengths. Dispersion mirror 14 directs excitation beam 24 to mirror 15, which reflects excitation beam 24 onto the objective optics. The objective optics, power monitor, laser line filter and spectral dispersion means are all discussed more fully herein.

The arrangement of FIG. 1A has the advantage that a user of the optical scanner system may connect and disconnect fibers coupled to different lasers such that any number of lasers may be used alone or changeably in different combinations. The system optics are pre-aligned and use of precision type fiber connectors allows for automatic fiber alignment.

Returning to FIG. 1, illumination beam 24 is directed by steering mirror 26 through laser line filter 28. A laser line filter is used to reduce transmission of light that is not of the excitation light wavelength. Laser line filters include band pass interference filters and absorption filters.

After passing through the laser line filter, illumination beam 24 impinges upon beam splitter 30. This element directs a portion of the beam through focus detection lens 32 and onto output detector 34. Output detector 34 monitors the power of illumination beam 24. In another embodiment, a beam splitter may split diverted beam 25 into two component beams, each beam composed of a subset of the wavelengths of beam 25. In this way the output of each of the lasers may be separately monitored. Alternatively, a shutter may be placed in front of each laser.

The light from excitation beam 24 that is not diverted to output detector 34 passes through zoom contractor/expander optics 36. These optical elements may be adjusted to shape the beam spot, allowing a variety of selectable beam spot sizes. The spot size can be selected by an electronic control element to produce a spot size that is optimized to the spot size of the targets to be scanned. For example, if the targets are spots on an array, the spot size may be matched to the array density or the spot size.

The light is focused by zoom expander/contractor and passes onto beam splitter optic 38. Beam splitter 38 is selected to direct the excitation wavelengths onto beam scanner 40. Beam scanner 40 produces a line scan of the focused beam. The beam scanner may be a galvanometer mirror, a rotating polygonal mirror, a resonant scanner, an acousto-optical scanner (e.g. a Bragg cell) or other known scanning optic.

As illustrated in FIG. 1B, a Bragg cell may be used to effect the beam spot line scan. In this embodiment, fixed mirrors 61, 62, 63 direct excitation beam 80 to Bragg cell 65 at an angle $\theta$ relative to the optical axis. RF drive 67 introduces an acoustic sound field within the Bragg cell. This acoustic field causes the excitation beam to be deflected through angle $\theta'$. This deflection produces a back and forth movement of the excitation beam along one axis. The optical scanner directs the beam to relay lenses 42 and 46 that keeps the focused laser light in register.

The scanning optic produces a back and forth scan of the beam of light. A motor translates the target substrate in a tangent direction. The scanned beam spot and the movement of the substrate in combination allow the system to scan in two dimensions a layer where the targets are located. This layer may be a substrate surface holding an array or a depth within a container containing discrete particles.

The light passes through relay lens 42 and is directed by steering mirror 44 through objective relay lens 46 and objective 48 and onto target substrate 50.

The target substrate may be any of a variety of substrates. This would include the presently used microscope slide arrays, microplate wells and storage phosphor screens. The microplate well format may present certain advantages, such as the ready adaptability to automated liquid and plate handling. The microplate dimensions may be used as a format for holders of other substrates, such as microscope slides. Storage phosphor screens may store a luminescent or radioactive signal and be subsequently analyzed by the present system. The present orientation of the optical elements in FIG. 1 illustrates a schematic for epi-illumination scanning.

When scanning a substrate, some focus method is required to focus the beam spot onto the substrate layer containing the array. This allows the optical system to direct the focused beam spot onto the layer containing the targets to be imaged. Such technology is disclosed in U.S. Pat. Ser. No. 09/296,145, hereby expressly incorporated for all purposes herein. In one method, specular reflection is used to determine the location of the underside of a solid transparent surface. Once the surface is localized, it is used as a reference point in relocating the beam waist to illuminate a target layer. The beam is moved relative to the target layer such that the beam waist scans through the target layer. This may be effected by moving the sample holding platform in the Z-axis. Power monitor 53 monitors the intensity of reflected light (e.g. specular reflection) focused by lens 51. At a reflection intensity maxima, the beam spot is focused on the reflective surface. This reference also discloses methods and devices in which optically detectable spots are etched, printed, or otherwise positioned at precise locations on the bottom of a sample holding substrate.

Light emitted from targets on the array is collected by the objective 48 and transmitted as a retrobeam to steering mirror 44. The emission retrobeam is transmitted to scanning mirror 40, which directs the beam to beam splitter optic 38. This optical element is selected such that the excitation beam is directed onto the beam scanner and objective while the fluorescent emission is directed to the detection optics.

As noted in the background section, previous optical systems have used a dichroic mirror to separate the illumination beam from the collected emission light. Selection of a dichroic becomes difficult if multiple lasers and fluorescent dyes are used. It is desirable to design alternative optical trains that allow multiple wavelengths to be used, without the need for bandpass-tailored filters.

The solution is to develop a design that eliminates the need for any dichroic mirrors or wavelength specific filters to be used to separate the illumination from the emission light.

Two factors allow for the separation of illumination light from emission light. The first is the diameter of the illumination beam is significantly smaller than the diameter of the collected emission light. The second is the fact that a collimated laser beam (i.e. a laser beam at a waist) and a collimated fluorescent beam will focus at different distances through a lens. This would allow the placement of a beam separator (e.g., central reflective disc positioned at an illumination beam waist) to direct the beam to the sample. This could be through passive direction (e.g. a simple pass through hole for the laser beam) or active direction (e.g. reflection). Surrounding the central portion of this optical element is an annular optical element that directs the collected fluorescent light to the detection optics. Again this direction could be passive (e.g. a transparent annulus allowing the beam to pass through the beam splitting optic). This is illustrated in the following examples.

FIG. 2 shows one embodiment of this optical element in which the central disc 38a on a dot mirror is a mirror comprised of a material that reflects a broad spectrum of wavelengths. This central disc is a broadly achromatic reflector and would reflect the excitation beam 24 irrespective of the component wavelengths selected for beam 24. Annularly surrounding central disc 38a is outer disc 38b. Outer disc 38b is comprised of a material that allows transmission of a broad spectrum of wavelengths. The excitation beam 24 is more narrow than the emission beam. An amount of emission light is reflected by the central disc 38a. The rest is transmitted through the transmissive outer annulus to the detectors. The amount of light which is lost is minimized by positioning the dot mirror at a waist of the illumination beam. The size of the dot mirror is selected relative to the size of the beam waist allowing for a minimal mirror size while still reflecting the beam. In this example, the illumination beam is actively directed (by reflection) to the sample and the collected fluorescent beam is passively directed (by transmission) to the detection optics. A mirror with a diameter sufficiently large to reflect the laser without clipping it but sufficiently small to minimize loss of the fluorescence beam should allow direction of the illumination beam and provide for some tolerance of element positioning.

A second example is shown in FIG. 4. In this example, a number of the optical elements, such as laser line filters, laser shutters, multiple lasers, etc., have not been shown for simplification. The laser 12 generates an illumination beam 24. This beam is focused by lens 91 into a beam waist b. Positioned at the waist b of illumination beam 24 is a hole 94 in mirror 92. The illumination beam 24 passes through the hole and onto lens 93. The illumination beam is collimated and is directed onto scanning optic 40, which produces the line scan of the beam. The beam is focused by relay lenses 42 and 46 to the objective lens 48 that focuses the illumination beam into a waist targeted onto sample substrate 50. The lenses used are achromats 90 that they may be used with a broad spectrum of wavelengths. The focused laser beam excites fluorescence from the sample. The fluorescent light is collected and transmitted as a retrobeam 60 back along the pathway of the excitation beam. The objective 48 acts as a light collector to collect the fluorescent emission. The light is transmitted as a collimated beam to relay lenses 42, 46 and onto scanning optic 40. The beam is directed through lens 93 and onto mirror 92. Mirror 92 reflects the collected fluorescent retrobeam 60 to the detection optics. The return fluorescent retrobeam is focused by lens 93 either upstream or downstream of the focus of illumination beam 24 (i.e. beam waist b). When the retrobeam 60 intersects mirror 92, beam 60 is significantly larger than the pinhole 94. While some of retrobeam 60 is lost through hole 94, most of the collected light is not lost.

In a scanning instrument, the beam scan is effected by a line scan of the excitation beam by an optical scanner. This requires sweeping the laser beam, relaying the image of the beam onto the objective, and focus of the scanning beam waist onto a target layer on the sample. Because a scanning beam would sweep past the inner annulus, the pinhole mirror should be located where the laser beam is not moving, i.e., upstream of the pinhole mirror.

In an example system, an objective with a focal length of 10 mm and a NA of 0.65 requires the laser beam radius to be 4 um at the focus. If lenses 91 and 93 in FIG. 4 each have a focal length of 10 cm, the combined 2 lens relay is spaced by $F_{91}+F_{93}=20$ cm. For lenses 91 and 93, the laser beam is chosen to focus at a distance $F_{eff}=\frac{1}{2} F=5$ cm [this turns out to give optimal laser beam/fluorescence beam separation.] For a helium/neon laser $\lambda=633$ nm. The incident beam radius w=142 $\mu$m is attained by the beam shaping optics. To have the beam waist imaged by lenses 91, 93 onto the scanning optic 40 the scanning optic is positioned at $F_{91}+F_{93}=20$ cm away from lens 93. The beam radius w at the scanning optic also 142 $\mu$m.

The beam size at the objective is calculated by back propagating the 4 $\mu$m focal spot. If objective 48 has a focal length of $F_{48}=10$ cm, and the focal spot radius is 4 $\mu$m, w is calculated to be w=504 $\mu$m. This is the size of the laser spot at the objective. From this the magnification of the relay lenses 42, 46 can be calculated and their focal lengths selected. Using the selected parameters the distance from lens 91 to mirror 92 is 5 cm; the distance between lens 91 and lens 93 is 20 cm; the distance between lens 93 and scanning optic 40 is 20 cm; the distance between scanning optic 40 and relay lens 42 is 2 cm, the distance between relay lens 42 and relay lens 46 is 9.1 cm; the distance between relay lens 46 and the objective lens 48 is 7.1 cm (assuming thin lenses); and the distance between the objective lens 48 and the sample 50 is 10 mm. This allows for a rather compact system that is able to rather efficiently collect the fluorescent light. This is one example of positioning of elements (using thin lens approximation) for FIG. 4.

The size of pinhole 94 must be sufficiently large so that the laser beam 24 is not blocked, and that an amount of alignment tolerance is allowed. The aperture radius is chosen to be 2.5×W where w is the laser beam radius at the location of the aperture. This is one example of how the size of the laser beam director is selected in relation to the diameter of the illumination beam waist. The diameter of the light director is sufficient to direct the laser beam with out clipping the beam resulting in energy loss while still sufficiently small to allow good fluorescence throughput. The location of the aperture may then be optimized to maximize the efficiency of collected fluorescence. This positioning results in minimal losses through the pinhole aperture and maximal reflection of collected fluorescence.

The source of fluorescence is assumed to be uniform over all angles. To calculate the integrated intensity at the pinhole mirror it is straightforward to calculate the magnification of the fluorescence beam from the objective to the location of the pinhole. This integral is then carried out in units scaled by the magnification. The pinhole 94 is located between relay lenses 91 and 93. At various distances from each lens, the laser beam size w is calculated, the pinhole aperture is set equal to 2.5w, and the fluorescence throughput is derived using the stated formula. At 15 cm (5 cm from lens 91, 15 cm from lens 93) the laser beam waist is at a minimum and the throughput losses are only a few percent. Although a slight improvement in efficiency of collection may be possible by locating the pinhole closer to lens 91, the described configuration does provide one working set up. In practice one single method of pinhole positioning is to simply locate the pinhole at the focus of the laser. The spacing requirements of the system requires that lens 91 and its mount be sufficiently far from mirror 92 to allow room for adjustments. The pinhole diameter for this example is 250 µm.

Returning to FIG. 1, the light directed to the detection optics first passes through long pass filter 52. Long pass filter 52 acts to filter out any excitation light and narrow the wavelengths, excluding light that is not of a selected wavelength range. The long pass filter is specifically selected to allow the wavelengths of emission beam 60 to pass through the filter. Thus different filters are needed depending on the component wavelengths of the emission light. A filter wheel (as shown in FIG. 3) is used to rotate into the emission beam path a long pass filter matched to the emission beam. In addition to rotation along the longitudinal axis, the filter wheel or tray may rotate within the plane of the angle of incidence, causing the impinging emission light to pass through a selectably greater thickness of the long pass filter (as explained in conjunction with FIG. 3). This may serve as a secondary method in which to adapt the filter to the specific selected wavelengths.

After passing through long pass filter 52, emission beam 60 is directed by steering mirror 54 through spatial filter lens 56. This lens focuses the collimated emission light through aperture 62 in spatial filter 58. Spatial filter 58 acts in combination with the light gathering optics and the focused illumination to limit the depth of field of the detection of the system. The excitation beam is focused such that the beam energy is concentrated into a beam spot directed at the target substrate. Outside of the focused beam spot, the excitation energy rapidly falls off. The emission light excited by the excitation beam is gathered by the objective optics and transmitted to the detection optics. The objective functions as a light collector and transmits light as a retrobeam to the detection optics. Emission light from outside the system depth of field (e.g. light that does not originate at or near the illumination beam focus) will be blocked from reaching the detector by the spatial filter.

The emission light which is focused through spatial filter 58 impinges upon beam splitter 64. Beam splitter 64 splits the emission light into wavelengths above and below a cutoff wavelength. Emission light above the cutoff wavelength is directed onto a first light detector 66. Light detector 66 may be a photomultiplier tube or other light detection optic. Emission light below a cutoff wavelength is directed onto a light detector 68. This light detector may again be a photomultiplier tube in photodiode or other light detection optic.

Detectors 66, 68 measure the fluorescent emission intensity of the fluorescent signal of the retrobeam. The detectors are in communication with data reader 90, which converts the signal from analog to digital. The signal is recorded by data reader 90 as a unit of fluorescence intensity. Although the detectors may contain any number of detection channels, two detectors and two detection channels are preferred. In the preferred embodiment, a spectral filter is used to selectively direct light below a selected cutoff wavelength to one detector and light above the selected cutoff wavelength to a second detector. The spectral dispersion device can be a prism, grating, or dichroic mirror. In this manner, multiple spectral dispersion devices and multiple detectors may be incorporated into the detection means for detection of fluorescence at different wavelengths from multiple fluorophores.

FIGS. 1C, 1D and 1E illustrate the use of a prism as the spectral dispersion device. In FIG. 1C, retrobeam 60 passes through aperture 60 and onto dispersion prism 71. In a system using a constant deviation dispersion prism, particular wavelengths may be directed onto a detector by rotation of the prism.

Prism 71 divides retrobeam 60 into component wavelengths represented by 83a, 83b, 83c. These component wavelengths 83a, 83b, 83c impinge upon segmented photodetector 73. Segmented photodetector may be a multichannel photomultiplier tube or charge-coupled device. This detector has a detecting surface 74 that detects the impinging light and produces an analog signal. For example, in a multichannel charge-coupled device, detecting surface 74 is made of a self-scanning metal-oxide semiconductor. The signal from the segmented detector is transmitted to a data reader as in FIG. 1.

In FIG. 1D a direct vision prism detector is shown. The use of a direct vision prism allows dispersion without deviating light at the central wavelength of the impinging light. Retrobeam 83 passes through aperture 24 and onto achromatic collimating lens 75. Collimating lens 75 collimates the light which then impinges upon direct vision prism 77. Direct vision prism is comprised of two or more prisms. Direct vision prism 77 as shown is comprised of a first prism 1 and a second prism 2. The prisms may be selected to transmit light in the range of 300–1100 nm.

The angles of surfaces a, b, c; the angle of the impinging light; and the material selected for prism composition will determine the amount of dispersion and the wavelength of the central undeviated light. Using a direct vision prism allows dispersion linearity and selection of wavelength range of detection. This range is matched to the fluorescent profile of the dyes used with the system. In one embodiment 300–1100 nm light will be measured by the present optical system. The central undeviated light could be one of the selected fluorescent dye emission wavelengths such as 667 nm or 695 nm. The positions of surfaces a,b,c align at angles n and m.

Collimated retrobeam 60 passes through direct vision prism 77 and is refracted into representative light beams 83d, 83e, 83f. Central wavelength 83e is undeviated. The light then impinges upon detecting surface 74 of segmented detector 73. The signal from the segmented detector 73 is transmitted to a data reader as in FIG. 1.

In another embodiment of the detection optics a prism is used in combination with a moveable mirror to allow measurement of different spectral components. This is seen in FIG. 1E. The emitted fluorescent light 60 is focused through aperture 62 of spatial filter 58. and through dispersion prism 101 which disperses the collected fluorescent light. Moveable mirror 103 reflects a first portion 109 of the dispersed collected light onto a first detector 68. A second spectral component of the collected fluorescent light 111, which is not reflected by mirror 103, will impinge on second detector 66. Mirror 103 is mounted on arm 105 that may be moved by stepper motor 107. This motor may be controlled by a central processor (not shown) that directs the positioning of the mirror. By changing the positioning of the mirror, different components of the dispersed light will impinge on each of detectors 66, 68. This effectively changes the cutoff wavelength that the system analyzes. By using a fixed dichroic in the detection system, the analysis of the collected light is limited to comparison of the light intensity above and below a single cutoff wavelength. In contrast, the detection configuration shown in FIG. 1E allows selection of the cutoff wavelength by positioning of mirror 103. When a dichroic mirror is used, the coating will not have 100% efficiency in separation of light at a cutoff wavelength. Some light that is intended to be reflected will be transmitted and some light which is intended to be transmitted will be reflected. This results in some background optical noise inherent in the use of dichroic elements. Both the configuration of FIG. 1 and the configuration of FIG. 1E allow the characterization of dyes by comparison of the ratio of two intensities of spectral components of the spectral emission. However, since the composition of the spectral components detected by the configuration shown in FIG. 1E is not fixed, a much larger set of dyes may be used and characterized by the system.

The combination of objective lens, collimating lens and aperture allows for a selected depth of field. Thus it is possible to use a sample container that is deeper than the focal depth (i.e., depth in which the focused laser light produces uniform illumination).

Fluorescent emission is gathered over a wide angle by the objective lens, which functions as a light collector.

An aperture in combination with an imaging lens will restrict the effective aperture of the lens and reduce aberration. However, a field stop could be ineffective to limit the depth of field, especially if the desire is to match the illumination volume to the collection volume. In contrast, the present invention uses a spatial filter to limit the depth of field. This spatial filter is positioned between the detector and the source of fluorescent emitted light. The spatial filter restricts the detection of light to rays of light emanating from a selected depth. This selected depth, as shown, is dependent on the geometry and placement of the spatial filter in relation to a lens. Matching the focal length of a lens to an aperture with specific geometry enables the present system to condition rays of emanating light to limit detection to a specific height of sample volume. The aperture is matched to the divergence of the lens to limit a depth of field. It is preferred that the spatial filter limit the depth of field to a depth of at least 25 $\mu$m. This use of a spatial filter is similar to the use of an aperture/focal lens combination in confocal microscopy to limit depth of field. The use of a confocal-type aperture as the spatial filter of the present system enables "macro-confocal" scanning, i.e. the optical interrogation with a focused beam of excitation light with the optical interrogation limited by a spatial filter to a selected depth of field. The size of the aperture and the placement of the aperture in relation to the focus lens in combination with the properties of the focused Gaussian beam will determine the selected depth of field. Thus, the use of a spatial filter allows optical interrogation of a limited depth of detection in a variety of containers. In each container the depth of field is limited to a selected depth. This limited depth of field creates an optical interrogation depth that may be similar to the depth of a capillary. This "virtual capillary" detection allows the present optical system to optically interrogate a container wherein the container has a depth much larger than the detected depth of field. This limits the detected background fluorescent substantially. The fluorescent light will be detected if it is emanating from a specific depth of field.

Detection of Targets

The scanning illumination beam excites fluorescence from targets on a substrate. The emitted fluorescence is the detected and recorded. The optical scanning means (i.e. galvanometer, Bragg cell, rotating polygonal mirror, etc.) moves the illumination to a new position to continuously illuminate new regions. The detection data is recorded by a data reader that records the measured emission intensity at preset intervals. The detection data capture is paced such that each illuminated columnar region detected partially overlaps another such region. The optical scanning and data collection continues in this manner of continuously illuminating and exciting a region from which fluorescent emission is detected and periodically recorded. These steps are continuously repeated during the scan.

The optical scanner follows a scan path in one direction that is transverse to the longitudinal axis of the scanned substrate and in the other direction along the length of the scanned substrate. The emission excited by the illumination is measured at selected intervals. The emission intensity from a beam spot illumination is measured and recorded. Preferably, the emission intensity is measured from overlapping beam spots.

The data acquisition and analysis may be effected in the manner described in U.S. Pat. No. 5,556,764 hereby expressly incorporated by reference herein.

In adapting microvolume fluorimetry to reading biological arrays on a substrate, the detection of targets on a substrate array allows for detection of individual dyes at specific locations. Because two dyes are not detected at a single location, the profile for the dyes in combination would not be observed unless non-specific binding occurred. Furthermore, improvements in system components, such as dichroic filter properties, reduction in electronic noise, improved calibration, etc. allows for recognition of greater number of dyes.

The present invention allows for analysis of a sample of biological fluid or substrate surface with a minimum of preparation. According to the present invention, a fluid is incubated with an excess amount of a binding agent that contains a fluorophore of known optical characteristics. The fluorescently-labeled binding agent is selected to react with binding sites present within the sample (e.g. array spots on a substrate). For example, a set of fluorescently labeled oligonucleotides (e.g. labeled cDNA from an expression assay) may be screened for hybridization to an array of DNA sequences, with each sequence located on a substrate at a discrete location. The labeled oligonucleotides and the target DNA at an array locus will hybridize if complementary and emit a fluorescent signal when analyzed by the apparatus of the present invention.

The method of the present invention does not require removal of unreacted fluorescently-labeled oligonucleotides (i.e. a homogenous assay may be performed). The oligonucleotides that are labeled with a fluorescent dye and are not hybridized to a DNA target on the array may be present as a background signal. Because the scanner limits detection to a selected depth of field, the localized concentration of detectable label present at an assay target spot would produce sufficient emission signal to allow detection over a background of unbound fluorescently labeled DNA fragments.

What is claimed is:

1. A device for analyzing sample arrays deposited on a substrate surface, the device comprising:
   a stage for holding the substrate, said stage movable along a first axis of said surface;
   at least one laser producing an illumination beam;
   focus optics in the path of the illumination light, said illumination focus optics focusing said illumination beam into a beam spot;
   a beam scanner for scanning said beam spot along a second axis of said surface;
   an objective lens, which gathers a percentage of light emitted from samples on said substrate and transmits collected light along an optical axis of said illumination beam to a light detector;
   a beam directing optic positioned between said laser and said objective lens said beam directing optic including an inner light directing element that directs the illumination beam to the objective lens and an outer light directing element disposed as an annulus about the inner light directing element, said outer light directing element directing collected emitted light at an angle relative to the optical axis of the illumination beam to detection optics;
   a spatial filter, acting in conjunction with the beam spot and objective lens to confine detection to a limited depth of field, said depth of field in a defined spatial relation to said substrate surface; and
   a light detection optics positioned to detect light which passes through said spatial filter.

2. The device of claim 1, further comprising:
   a beam splitting optics, positioned between said spatial filter and said light detector, wherein said beam splitting optics splits collected light into two spectral components that are separately detected by the light detection optics.

3. The device of claim 2, further comprising:
   a computer that characterized said collected emitted light by comparing ratio of measured intensity of each spectral component.

4. The device of claim 1, further comprising:
   at least one optical filter positioned between said laser and said focus optics such that said illumination beam passes through the filter.

5. The device of claim 1, wherein the at least one laser includes a first laser and a second laser and the device further comprises beam combining optics to combine beams produced by said first and second laser to produce the illumination beam.

6. The device of claim 1, wherein said beam scanner is one of a group comprising a galvanometer, a Bragg cell, a resonant scanner and a rotating polygonal mirror, said device moving said beam spot in a line scan.

7. The device of claim 1, further comprising:
   beam spot focusing optics, said optics detecting when the beam spot is focused onto said substrate surface.

8. The device of claim 1, wherein said inner light directing optic is positioned proximate to a waist of the illumination beam.

9. A system for detecting discrete fluorescent targets, the system comprising:
   at least one laser producing an illumination beam;
   illumination focus optics in the path of the illumination beam, said illumination focus optics focusing said illumination beam into a beam spot;
   a light directing optic positioned between said focus optics and said beam scanner, said light directing optic including a central light directing optic surrounded by an outer light directing annulus, wherein the central light directing optic has a width matched to a waist of focused illumination beam and said central optic directs the beam spot to said layer;
   an objective lens, which focuses the beam spot onto the sample, thereby exciting fluorescent emission, said objective further collecting said fluorescent emission and directing as a retrobeam said emission light to said outer light detecting annulus, wherein said outer annuls directs collected fluorescent light onto detection optics;
   a spatial filter that confines detection to a limited depth of field;
   a light detector positioned to detect light which passes through said spatial filter; and
   a computer receiving signals from said detector, said computer analyzing said signals to recognize discrete targets.

10. The system of claim 9, wherein the light directing optic is a dot mirror with a transparent annulus, wherein the dot mirror directs the illumination liqht to the sample and the transparent annulus allows collected fluorescent light to pass onto the detection optics.

11. The system of claim 9, wherein the light directing optic is a mirror with a beam pass through hole located proximate to a center of the mirror, wherein the mirror is positioned such that the illumination beam may pass through the hole while the collected emission light is reflected by the mirror onto detection optics.

12. The system of claim 11, wherein the hole is positioned proximate to a waist of the illumination beam.

13. The system of claim 9, further comprising,
   at least one laser line filter positioned between said laser and said focus optics such that said illumination beam passes through the laser line filter.

14. The system of claim 9, further comprising shutters placed between the laser and the illumination focus optics.

15. The system of claim 9, further comprising a beam scanner that scans the beam spot through a layer in a sample container holding the fluorescent targets.

16. The system of claim 15, wherein said beam scanner includes a device selected from the group comprising a galvanometer, a Bragg cell, a resonant scanner and a rotating polygonal mirror, said device moving said beam spot in a line scan.

17. The system of claim 16, wherein the beam scanner further comprises a stepper motor for translating the sample in a direction tangent to said line scan.

18. The device of claim 9, further comprising:
   a focusing system for targeting the beam spot onto the layer on the sample.

* * * * *